United States Patent [19]
Garry et al.

[11] Patent Number: 5,620,859
[45] Date of Patent: Apr. 15, 1997

[54] METHOD TO AID IN THE DIAGNOSIS OF SILICONE RELATED DISEASE

[75] Inventors: Robert F. Garry; Scott A. Tenenbaum; Douglas R. Plymale, all of New Orleans, La.

[73] Assignee: Administrators of the Tulane Educational Fund, New Orleans, La.

[21] Appl. No.: 320,889

[22] Filed: Oct. 5, 1994

[51] Int. Cl.$^6$ .................. G01N 33/53; G01N 33/564
[52] U.S. Cl. .................. 435/7.9; 435/7.1; 435/7.92; 435/7.94; 435/7.95; 435/975; 436/501; 436/506; 436/509; 436/518; 436/72; 436/811
[58] Field of Search .................. 435/7.1, 7.9, 7.92, 435/7.94, 7.95, 975; 436/501, 518, 543, 72, 811, 506, 509, 63; 530/387.1, 389.8

[56] References Cited

U.S. PATENT DOCUMENTS

| | | | |
|---|---|---|---|
| 4,428,048 | 1/1984 | Berlin | 395/775 |
| 5,312,620 | 5/1994 | Ribi | 424/78.31 |

OTHER PUBLICATIONS

Tenenbaum et al., Arthritis and Rheumatism, 36 (9 Suppl), Abstract S118 (1993) "Identification of a novel antigen recognized by silcone implant recipients".

Teuber et al., Journal of Autoimmunity, 6, pp. 367–377 (1993) "Anti–collagen Autoantibodies are Found in Women with Silicone Breast Implants".

Kossovsky et al., Arch Pathol lab Med. 118, pp. 686–693 (1994) "Silicone Breast Implant Pathology".

Dauber, J. H., Rossman, M. D., Pietra, G. G., Jimenez, S. A., Daniele, R. P. Experimental silicosis. *American Journal of Pathology*, 1980; 101: 595–607 and FIGS. 1–5.

Kossovsky, N. et al: Surface dependent antigens identified by high binding avidity of serum antibodies in a subpopulation of patients with breast prostheses. *Journal of Applied Biomaterials* 1993; 4: 281–288.

Lilla, J. A., and Vistnes, L. M.: Long–term study of reactions to various silicone breast implants in rabbits. *Plast & Reconstr. Surg.* 1976; 57: 637–649.

Naim, J. O., Lanzafame, R. J. and van Oss, C. J: Immuno–logical adjuvancy of silicone–gel *Immunological Investigations* 1993; 22: 151–161.

Nalbandian, R. M., Swanson, A. B., Maupin, B. K.: Long–term silicone implant arthroplasty. *Journal of the American Medical Assn.* 1983; 250: 1195–1200.

Nosanchuk, J.S.: Injected dimethylpolysiloxane fluid: A study of antibody and histologic response, *Plast. & Reconstr. Surg.* 1968; 42: 562–566.

Picha, G. J. and Goldstein, J.A.: Cellular response to silicone. *Plast. & Reconstr. Surg.* 1991; 87: 490–500.

Tenenbaum, S. A., Silveira, L. H., Martinez-Osuna, P., Cuellar, M. L., Garry, R. F. and Espinoza, L. R.: Identification of a novel autoantigen recognized in silicone–associated connective tissue disease. *American College of Rheumatology* 1992.

Wolf, L. E., Lappe, M. Peterson, R. D. and Ezrailson, E. G.: Human immune response to polydimethylsiloxane (silicone): screening studies in a breast implant population. *The FASEB Journal* 1993; 7:1265–1268.

*Primary Examiner*—Lora M. Green
*Attorney, Agent, or Firm*—Arnold, White & Durkee

[57] ABSTRACT

A process to aid in the diagnosis of silicone related disease in which a correlation between silicone related disease and the presence of antibodies that bind to partially polymerized acrylamide is disclosed.

5 Claims, No Drawings

METHOD TO AID IN THE DIAGNOSIS OF SILICONE RELATED DISEASE

FIELD OF THE INVENTION

The present invention is directed to a process and a kit for diagnosing silicone related disease (SRD). The process comprises obtaining a sample of body fluid from a patient and testing the sample for the presence of anti-polymer antibodies reacting to partially polymerized acrylamide as an antigen. The presence of anti-polymer antibodies indicates SRD if the patient has a polymeric implant, or a pre-disposition to SRD if the patient has no implant.

BACKGROUND OF THE INVENTION

Silicones are entirely synthetic polymers containing a repeating silicon-oxygen (Si—O) backbone with organic groups attached directly to the silicon atom through a carbon bond. The most common form of silicone is polydimethylsiloxane (PDMS) and has a repeating unit of $(CH_3)_2SiO$.

Silicone polymers have, until recently, been considered biologically and immunologically inert, and for this reason are included as exterior coatings or components of most medical devices that are surgically implanted into humans. Some examples of silicone-containing devices include hip replacements, catheters, mandibular prostheses, and breast implants. It is estimated that more than 2 million women in the United States have been recipients of silicone implants for augmentation mammoplasty and breast reconstruction following cancer surgery.

However, as devices such as silicone breast implants have become more widely used, there has arisen increased concern that silicone may be neither biologically nor immunologically inert. Silicone can be formed into fluids, gels or solids based on the degree of linear, branched, and crosslinked subunits. The degree of crosslinking dictates the consistency of the resulting silicone, which can vary from a clear gel to a white opaque elastomer. The crosslinked polymers form a loose intertwining matrix which retains the remaining silicone fluid. The lack of chemical integrity of this complex is suspected to permit "gel bleed" of silicone fluid slowly out of the matrix. Impurities such as catalyst, short linear polymers and small cyclics can remain depending on the stringency of the purification technique employed.

Approximately 10% of patients who receive medical devices containing silicone polymers experience complications including inflammation, severe muscle pain, or overt rheumatic (autoimmune) disease. Recently, silicone implants have been linked to multiple sclerosis-like symptoms, particularly in patients whose implants have ruptured. Yet, a portion of the approximately 2 million women in the United States who have received silicone gel filled breast implants have complications such as infection, capsular contraction, leakage, and rupture (Touchette, 1992). Additionally, some breast implant recipients experience a syndrome characterized by symptoms which include fibromyalgia, sicca syndrome, lymphadenopathy, contracture, sclerodactyly, alopecia, edema, telangiectasias, changes in pigmentation, recurrent fever, skin rash, and chronic fatigue (Brozena et al., 1988; Seleznick et al., 1991; Vasey et al., 1991; Copeland et al., 1993; Spiera and Kerr, 1993; Spiera et al., 1994). This syndrome, which also afflicts recipients of other silicone-containing medical devices, was previously termed human adjuvant disease (HAD) (Miyoshi et al., 1964; Miyoshi et al., 1973). Individuals surgically implanted with various devices containing silicone may also develop arthritic and dermatologic conditions that present autoimmune-like diseases, such as systemic sclerosis (scleroderma) or Sjögren's syndrome (Brozena et al., 1988; Vasey et al., 1991; Spiera et al., 1994). Studies implicating silicone-containing medical devices in autoimmune diseases, however, have been met with considerable skepticism (Gabriel et al., 1994).

Complications occurring after implantation of silicone-containing medical devices may generally fall in two categories:

1) Atypical Connective Tissue Disease (ACTD)/Atypical Rheumatic Syndrome(ARS)/Nonspecific Autoimmune Condition (NAC). Symptoms include tightness of skin, contracture, sclerodactyly, alopecia, oedema, telangiectasias, rash, and changes in pigmentation. These symptoms have been frequently associated with silicone breast implants, but occur also in recipients of other silicone-containing medical devices.

2) Overt autoimmune diseases. Some investigators have reported that recipients of breast implants are more likely than non-implanted individuals to develop autoimmune diseases such as systemic lupus erythematosus or scleroderma. Increased levels of previously defined autoantibodies (SS-A, SS-B, Sm, etc.) have also been observed.

Exposure to silicone breast implants can result in the manifestation of symptoms and complications that collectively are dissimilar from previously recognized or defined rheumatological diseases, and therefore, may be uniquely identifiable with the appropriate diagnostic tests. Nevertheless, the systemic nature and relatively nonspecific symptoms of the diseases, particularly undifferentiated rheumatic diseases and SRD, often make the diseases difficult to diagnose and difficult to distinguish. An assay method which would enable the clinician to distinguish and discriminate between undifferentiated rheumatic diseases and SRD is highly desired.

Surgical implants have benefits that extend from prolongation of life to cosmetic enhancement. Implants also have associated risks, and these unknown risks motivate some people to forego implants, even though the benefit may outweigh the risk. Likewise, removal of existing implants may involve expense, pain, disfigurement, disability and death. A diagnostic test that would help an implant candidate balance the benefit and the risk of his/her implant is badly needed.

SUMMARY OF THE INVENTION

The present invention is directed to a process and a kit for diagnosing silicone related disease (SRD). The process comprises obtaining a sample of body fluid from a patient and testing the sample for the presence of anti-polymer antibodies reacting to partially polymerized acrylamide as an antigen. The presence of anti-polymer antibodies indicates SRD if the patient has a polymeric implant, or a pre-disposition to SRD if the patient has no implant.

Additional objects, features, and advantages will be apparent in the written description which follows.

DETAILED DESCRIPTION OF THE PREFERRED EMBODIMENTS

In characterizing autoimmune responses in various systemic autoimmune diseases, including scleroderma, Sjögren's Syndrome, and systemic lupus erythematosus (SLE), we use immunoassays. Immunoassay techniques are extremely sensitive and specific, and in using these methods we identified a novel polymeric antigen that is recognized by serum antibodies from over 50% of persons with silicone breast implants who display systemic "autoimmune-like" symptomatology. We have developed an extremely sensitive immunoblot assay (Line blot) that is capable of detecting these anti-polymer antibodies (APAs). Our results indicate that an APA immunological response may contribute to complications from implanted silicone polymer-containing devices.

These results provide the first definitive evidence that silicone breast implants are capable of inducing an immunological response that is diagnostically testable. The detection of this immunological response provides us with a unique opportunity to develop a serological test that has broad clinical applications.

Anti-polymer antibodies appear to be a reliable predictor of the autoimmune-like complications associated with silicone breast implants. Our work is the first study to provide an unambiguous result indicating that silicone is not immunologically inert. Our results also identify a distinguishing feature that may be of diagnostic and prognostic value in treating these individuals. Moreover, our results form the basis for a test that if properly developed could find widespread medical and commercial use in the biotechnology industry. The test could be used to monitor immunological responses to silicone-containing medical devices. In the future, this is likely to be an important criterion for devices used in the medical industry. This could afford the development of alternative polymer forms of silicone specifically formulated so as not to elicit immune reactivity.

Surgical implants have benefits that extend from prolongation of life to cosmetic enhancement. Implants also have associated risks. It is known that some people produce anti-polymer antibodies, but do not have implants. In those people, placement of an implant might aggravate latent problems that are manifested by anti-polymer antibodies. The anti-polymer test can help implant candidates to evaluate risk associated with their implant and to decide either to forego the benefit to avoid the risk, or to accept the risk to obtain the benefit.

For those people who already have implants, the test would be useful in determining whether to remove the implant. A negative anti-polymer test would provide some assurance that the risk is at least not immediate, and with continued monitoring the pain, expense, disfigurement and medical risk of surgical removal could be avoided. A positive test would provide some assurance that removal is appropriate.

Definitions

Before proceeding further with the description of various specific embodiments of the present invention, a number of terms will be defined. A variety of assay techniques in which the object of the present invention can be achieved are also described.

The term "analyte" refers to either the polymer antigen or the anti-polymer antibody.

As used herein, "test sample" or "body fluid sample" typically refer to a naturally occurring or artificially formed liquid test medium suspected of containing the analyte of interest. The test sample is generally a biological fluid or a dilution thereof. Biological fluids from which an analyte can be determined include serum, whole blood, plasma, body fluid, saliva, amniotic and cerebrospinal fluids, and the like.

The term "indicator reagent" refers to an assay reagent comprising a detectable label directly or indirectly attached to a specific binding member which is capable of directly or indirectly binding to the analyte to indicate the presence, absence or amount of the analyte. A variety of different indicator reagents can be formed by varying either the label or the specific binding member. In general, the indicator reagent is detected after it has formed a complex with either the analyte or a complementary specific binding member, but the unbound indicator reagent can also be detected.

The term "specific binding member" refers to a member of a specific binding pair, i.e., two different molecules wherein one of the molecules through chemical or physical means specifically binds to the second molecule. In addition to antigen and antibody specific binding pairs, other specific binding pairs include biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders, protein A and antibodies, protein G and antibodies, and the like. Furthermore, specific binding pairs can include members that are analogs of the original specific binding member, for example an analyte-analog. If the specific binding member is an immunoreactant it can be, for example, an antibody, antigen, hapten, or complex thereof. If an antibody is used, it can be a monoclonal or polyclonal antibody, a recombinant protein or antibody, a mixture(s) or fragment(s) thereof, as well as a mixture of an antibody and other specific binding members. The details of the preparation of such antibodies and their suitability for use as specific binding members are well-known to those skilled in the art.

The term "label" refers to any substance which is attached to a specific binding member and which is capable of producing a signal that is detectable by visual or instrumental means. Various suitable labels for use in the present invention can include chromogens; catalysts; fluorescent compounds; chemiluminescent compounds; radioactive labels; direct visual labels including colloidal metallic and non-metallic particles, dye particles, enzymes or substrates, or organic polymer latex particles; liposomes or other vesicles containing signal producing substances; and the like.

The term "signal producing component" refers to any substance capable of reacting with another assay reagent or the analyte to produce a reaction product or signal that indicates the presence of the analyte and that is detectable by visual or instrumental means. "Signal production system," as used herein, refers to the group of assay reagents that are needed to produce the desired reaction product or signal. For example, one or more signal producing components can be used to react with a label and generate the detectable signal, i.e., when the label is an enzyme, amplification of the detectable signal is obtained by reacting the enzyme with one or more substrates or additional enzymes to produce a detectable reaction product.

The term "capture binding member" refers to a specific binding member which can directly or indirectly bind the analyte or indicator reagent and which is bound or is capable of being bound to a solid phase, or is capable of being precipitated, such that the capture binding member can be separated from the test sample and other assay reagents by any means. The term "capture reagent" refers to a capture binding member which is directly or indirectly attached to a solid phase material to enable the separation of the capture binding member, and analyte or indicator reagent that is bound thereto, from unbound analyte and assay reagents.

Typically, the attachment of the capture binding member to the solid phase material is substantially irreversible and can include covalent mechanisms. The capture reagent of the present invention, however, is not limited to a capture binding member bound to an insoluble solid phase material. In an agglutination assay, the capture binding member of the capture reagent can be bound to a soluble carrier material such as bovine serum albumin.

The term "solid phase material" refers to any suitable chromatographic, bibulous, porous or capillary material or other conventional solid material, well-known to those skilled in the art, used to immobilize specific binding members. In the present invention, the solid phase material can include a fiberglass, cellulose or nylon pad for use in a flow-through assay device having one or more layers containing one or more of the assay reagents; a dipstick for a dip and read assay; a test strip for chromatographic (e.g., paper or glass fiber) or thin layer chromatographic (e.g., nitrocellulose) techniques in which one or all of the reagents are contained in separate zones of a single strip of solidifies material; or an absorbent material well-known to those skilled in the art. The solid phase material can also include, without limitation, polyacrylamide beads, polystyrene beads or tubes, magnetic beads, a microtitre plate or a glass or plastic test tube.

Natural, synthetic, or naturally occurring materials that are synthetically modified can be used as a solid phase material. These materials include polysaccharides, cellulose materials such as paper and cellulose derivatives such as diazobenzyloxymethylcellulose, nitrocellulose, 2-aminophenylthioetheylcellulose, and cellulose acetate; silica; silicon particles; inorganic materials such as deactivated alumina, or other inorganic finely divided material uniformly dispersed in a porous polymer matrix, with polymers such as vinyl chloride, vinyl chloride polymer with propylene, and vinyl chloride polymer with vinyl acetate; cloth, both naturally occurring (e.g., cotton) and synthetic (e.g., nylon); porous gels such as silica gel, agarose, dextran, and gelatin; polymeric films such as polyacrylates; protein binding membranes; and the like. The solid phase material should have reasonable strength or strength can be provided by means of a support, and it should not interfere with the production of a detectable signal.

Blocking is a term that describes procedures used to prevent nonspecific adsorption of immunological reagents to a solid phase material. Blocking methods are well known to those skilled in the art.

Optionally, the specific binding member of the capture reagent can be affixed to particles, e.g., microparticles. These microparticles can serve as the solid phase material and be retained in a column, suspended in a mixture of soluble reagents and test sample, or retained and immobilized by another solid phase base material. By "retained and immobilized" is meant that the microparticles associated with the solid phase base material are not capable of substantial movement to positions elsewhere within that material. The microparticles can be selected by one skilled in the art from any suitable type of particulate material including those composed of polystyrene, polymethylacrylate, polypropylene, polytetrafluoroethylene, polyacrylonitrile, polycarbonate, or similar materials. The size of the microparticles is not critical, although it is preferred that the average diameter be smaller than the average pore size of the solid phase base material if such is used.

The homogeneous assay configurations do not require the separation of the test solution and the indicator reagent prior to the detection of the indicator reagent or binding complexes. This broad classification includes many formats such as agglutination and precipitation assays, as well as others known to those skilled in the art for the detection of analytes. Both direct and indirect agglutination assays can be performed.

The term "ancillary specific binding member" refers to a specific binding member used in addition to the capture binding member and the indicator reagent which becomes a part of the detectable binding complex. One or more ancillary specific binding members can be used in an assay. For example, an ancillary specific binding member can be used in an assay where the indicator reagent is capable of binding the ancillary specific binding member which is in turn capable of binding the analyte.

The homogeneous assay configurations do not require the separation of the test solution and the indicator reagent prior to the detection of the indicator reagent or binding complexes. This broad classification includes many formats such as agglutination and precipitation assays as well as others known to those skilled in the art for the detection of analytes. Both direct and indirect agglutination assays can be performed.

The object of present invention can be achieved by a variety of binding assay configurations and formats which enable the detection or measurement of APA antibody to diagnose, stage or predict the course of rheumatic disease. The APA antibody were found to be readily detectable in urine samples by means of binding assays which are generally categorized into one of two major classes, homogeneous and heterogeneous assays. These assays may be further divided into sandwich and competitive assay formats, and variations thereof.

In a solid phase sandwich assay, the capture reagent typically involves a specific binding member which has been bound to a solid phase material. For example, the specific binding member can be an immobilized antibody which will bind to an antigen-analyte in the test sample, or the specific binding member can be an immobilized antigen which will bind to an antibody-analyte in the test sample. The capture reagent is contacted to a test sample suspected of containing the analyte, and to an indicator reagent comprising a second specific binding member that has been labeled, for example, a labeled anti-analyte antibody. The reagents can be mixed simultaneously or added sequentially, either singly or in combination. A binding reaction results in the formation of a capture reagent/analyte/indicator reagent complex immobilized upon the solid phase material. The assay can also comprise the step of separating the resultant complex from the excess reagents and test sample. The complex retained on the solid phase material is detected by examining the solid phase for the indicator reagent. If analyte is present in the sample, then label will be present on the solid phase material. The amount of label on the solid phase is a function of the amount of analyte in the sample.

The homogeneous assay configurations do not require the separation of the test solution and the indicator reagent prior to the detection of the indicator reagent or binding complexes. This broad classification includes many formats such as agglutination and precipitation assays as well as others known to those skilled in the art for the detection of analytes. Both direct and indirect agglutination assays can be performed.

It will be appreciated by those skilled in the art that the selection of any given label, binding member, ancillary binding member or solid phase material is generally not critical to the present invention. The materials are chosen to optimize the results provided by the chosen assay configuration.

The methods of the present invention can also be carried out using competitive assay formats. In a solid phase competitive assay, the capture reagent again typically involves a specific binding member which has been affixed to a solid phase material and which is contacted with both test sample and an indicator reagent. The indicator reagent, however, can be formed from an analyte or analyte-analog which has been conjugated with a label. A binding reaction occurs and results in the formation of complexes of (1) immobilized capture reagent/analyte complex and (2) immobilized capture reagent/indicator reagent complex. Alternatively, the immobilized specific binding member can be an analyte or analyte-analog with which the test sample analyte competes for binding to the indicator reagent. In the competitive assay, the amount of label on the solid phase is inversely related to the amount of analyte in the sample. Thus, a positive test sample will generate a decrease in signal.

In the present invention, a solid phase sandwich assay is used to detect the presence or amount of anti-polymer antibodies in body fluid. Typically, the capture reagent is polymer antigen, or individual subunits thereof, immobilized upon a solid phase material. After the antigen is affixed to the solid phase material, the body fluid sample is incubated with the capture reagent for a period of time and under conditions sufficient for the formation of specific complexes between anti-polymer antibodies in the body fluid and the polymer antigen. The solid phase material can then be washed with a buffer solution to remove unbound test sample. The buffer solution can be any buffer conventionally known and used by those skilled in the art. The resultant complexes are then incubated with an indicator reagent, such as a second labeled polymer antigen, for a period of time and under conditions sufficient for the formation of a ternary complex. The unreacted indicator reagent is then removed by again washing the solid phase with a buffer solution. The quantity of indicator reagent bound to the solid phase is then measured by a technique compatible with the label component of the indicator reagent. If quantitated, the amount of indicator reagent bound to the solid phase is proportional to the quantity of body fluid anti-polymer antibody bound to the solid phase.

In addition to nitrocellulose, we have successfully used polyvinylidene diflouride (PVDF) and nylon as alternative membrane sources in the APA line blot assay as well as adapting the assay to a standard 96-well polystyrene enzyme linked immunosorbent assay (ELISA) format. Although the APA line blot is described in detail in this patent request and was found to be the most useful, the APA line blot should be amenable to adaptation to other immunological assays including latex agglutination, antibody capture assays, radioimmunoprecipitation assays (RIPA), polystyrene bead based enzyme immunoassays (EIA), and particle concentration fluorescence immunoassays (PCFIA).

By observing the results of anti-polymer antibody assays, an accurate diagnosis or differentiation between undifferentiated rheumatic diseases and SRD provides a means to predict the immediate future course of the disease. In the present invention, the results of the assays used to detect polymer antigens and antibodies are interpreted as described below.

Test results for assays detecting the presence or amount of anti-polymer antibody in a test sample.

The results of the anti-polymer antibody (APA) test are interpreted as follows. If:

(1) said patient has no polymeric implant, then the presence of said antibody indicates that the patient has a condition predisposing to SRD;

(2) said patient has a polymeric implant, then the presence of said antibody indicates that the patient has SRD;

(3) said patient has a polymeric implant, then the absence of said antibody indicates that the patient does not have SRD;

(4) said patient has a polymeric implant and has been previously diagnosed as having undifferentiated rheumatoid disease selected from the group consisting of SRD, atypical connective tissue disease, atypical rheumatic syndrome, nonspecific autoimmune condition, or overt autoimmune diseases (such as CREST), then the presence of said antibody indicates said rheumatoid disease is SRD.

(5) said patient has no polymeric implant and has previously been diagnosed as having an undifferentiated rheumatoid disease selected from the group consisting of SRD, atypical connective tissue disease, atypical rheumatic syndrome, nonspecific autoimmune condition, or overt autoimmune diseases (such as CREST), then the absence of said antibody indicates said rheumatoid disease is predisposing to SRD.

The exemplary assays of the present invention typically involve the addition and incubation of several different reagents. A variety of different buffer and washing solutions can be used to stabilize the reagents and to remove excess reagents or test sample from the reaction. As is well-known to those skilled in the art, modifications can be made in the buffer and washing solutions, as well as in the reaction times.

The assay reagents can also be provided in kit form. A test kit to detect anti-polymer antibody would typically contain a solid phase material upon which polymer antigen is immobilized and optionally include an appropriate supply of a suitable indicator reagent, buffers and washing solutions. A test kit to detect polymer antigen would typically contain a solid phase material upon which anti-polymer antibody is immobilized or upon which components of the patient's test sample can be immobilized (e.g., direct immobilization of the antigen upon the solid phase), and optionally include appropriate amounts of a suitable indicator reagent, buffers and washing solutions. Other components such as stabilizers and preservative agents can also be present in the kit and/or in the reagents.

Methods generally known to those skilled in the immunological arts are described in Antibodies:. *A Laboratory Manual* by Ed Harlow and David Lane (1988). Cold Spring Harbor Laboratory. Chapters 12 and 14 of this book are hereby incorporated by reference.

The following examples describe, in detail, preferred assays according to the present invention. The examples are provided to further illustrate the advantages of the present invention and the specific experiments performed.

Materials and Methods

Sample Collection

Serum from each subject or control were collected and stored at −20° C. under the supervision of Dr. Luis Espinoza, Dr. David Burns or Dr. Oscar Gluck until shipment on ice by overnight carrier. Samples were stored at −20° C. or 4° C. until time of testing.

Anti-Polymer Antibody (APA) Line Blot Analysis

Partially polymerized acrylamide (PPA) was prepared by mixing 2.5 ml Acryl:Bis (37.5:1), 8.5 ml $H_2O$ and 3.5 ml of 1.5M Tris. This 5% acrylamide solution was cross-linked with 100 μl of 0.01% ammonium persulfate and 20 μl TEMED (N,N,N'-Tetramethylethylenediamine), and allowed to solidify for 15 minutes in a 60 ml beaker. The PPA remains on top as a slightly viscous liquid.

Aliquots of polymer were sequentially diluted 5, 25, 125, 625, and 3,125 fold, applied to nitrocellulose membranes and allowed to air dry The nitrocellulose membranes were then cut into strips and incubated for 1 hour with blinded test sera diluted 1:400 in Western blot blocking buffer. Bound IgG or IgM were visualized by a series of reactions using biotinylated goat anti-human IgG or anti-human IgM immunoglobulin, avidin-conjugated horseradish peroxidase, and the enzyme substrates hydrogen peroxide and 4-chloro-1-naphthol.

Each anti-polymer antibody (APA) strip lot (28 strips) was run with a negative, weak-positive, and strong-positive control. The weak-positive control served to standardize the enzymatic developing portion of the assay. Strip lots were standardized based on reactivity of control sera which subsequently were used to assess the level of reactivity of test sera. Results were given on a scale from 0–3 with 3 being defined as ≧75% of the strong-positive control, 2 being defined as ≧25%, but <75% of the strong-positive control, 1 being defined as >10%, but <25% of the strong-positive control, and 0 being defined as <10% of the strong-positive control.

Autoantibody Westen Blot Assays

Nitrocellulose strips containing electrophoretically separated and transferred human epithelial cells (HEp-2) proteins were incubated with blinded subject and control sera at a concentration of 1:100 for 1 hour. Bound immunoglobulin were visualized by a series of reactions using alkaline phosphatase conjugated goat anti-human IgG, and the enzyme substrates tetra nitroblue tetrazolium chloride and 5-bromo-4-chloro-3-indlyl phosphate in aqueous dimethylformamide.

Statistical Analysis

Statistical analysis of the accumulated data was performed using StatView (Brainpower, Inc. Calabasan, Calif.) or Epilnfo software (Ludwig Cancer Institute, Sao Paulo, Brazil) and interpreted by Dr. Patricia L. Ryder, M.D., M.P.H., Tulane University, School of Public Health and Tropical Medicine.

F'ab digest

F'ab digestion was performed using a commercial F'ab digestion kit (Pierce Inc.) according to manufacturer instructions and utilized immobilized papain and protein A column purification.

Total immunoglobulin concentration immunodiffusion assay

Total IgG, IgA, and IgM was determined using a commercial immunodiffusion assay according to manufacturer instructions (The Binding Site Limited, Birmingham, England). Total IgG, IgA or IgM was determined by adding 5 ml of patient or control sera to wells in agar containing isotype-specific anti-human antibodies. After 48 hours zones of precipitation were measured and total immunoglobulin isotype concentration calculated from a standard curve.

Results

EXAMPLE 1

The bis-acrylamide to acrylamide ratio was varied from 1:5 up to 1:40 in increments of 5. Mixtures with a ratio of 1:20 bis-acrylamide:acrylamide or greater bound anti-polymer antibody from a highly positive sample, and did not bind anti-polymer antibody from a negative sample. The most specific binding of anti-polymer antibody was obtained with a ratio of 1:37, which is the ratio of the monomers provided in the stock acrylamide obtained from the manufacturer. This ratio was used in all experiments described below.

The detection of anti-polymer antibodies (APAs) on the HIV-1 Western blot.

Evidence suggesting that silicone-containing medical devices induce autoimmune conditions is currently the subject of an active controversy in the biotechnology industry (Angell, 1992; Touchette, 1992). It is clear that some recipients of breast implants or other silicone-containing medical devices do experience complications, but the basis for this condition is not known. There is conflicting evidence as to whether silicone can elicit any immune response (Angell, 1992; Touchette, 1992). It was hypothesized that patients experiencing complications related to silicone gel filled implants may produce serum antibodies to common autoantigens recognized by patients with other autoimmune conditions in unique patterns. Using a combination of these Western blot assays, we tested sera from individuals experiencing complications associated with exposure to silicone. We found no appreciable increase in the incidence of serum antibodies reactive to known autoantigens. However, on both Western blot assays, approximately 50% of the silicone exposed individuals had serum antibodies that reacted to what appeared to be a high molecular weight protein that banded at the top of the Western blot strips. Immunological reactivity was clearly visible on these strips when assayed with sera from individuals exposed to silicone, but varied in intensity from strongly reactive to moderately reactive to non-reactive. Reactivity was not visualized when the strips were blotted with healthy blood donor sera, SLE sera or HIV strong-positive control sera.

Characterization of indeterminate results from silicone exposed individuals.

It was speculated that the indeterminate band at the top of the HIV-1 Western blot may be an artifact of the Western blot technique. This theory was tested by performing the Western blot transfer with a polyacrylamide gel that contained no protein. Sera from silicone exposed individuals that was positive for the indeterminate band reacted to a similar band on these "holistic" Western blot strips.

The unique band was determined not to be a protein, but a polymer composed of partially polymerized acrylamide (PPA). Polyacrylamide gels are formed as a result of free-radical polymerization of acrylamide monomers into long chains that are cross-linked to one another by bisacrylamide, as shown below.

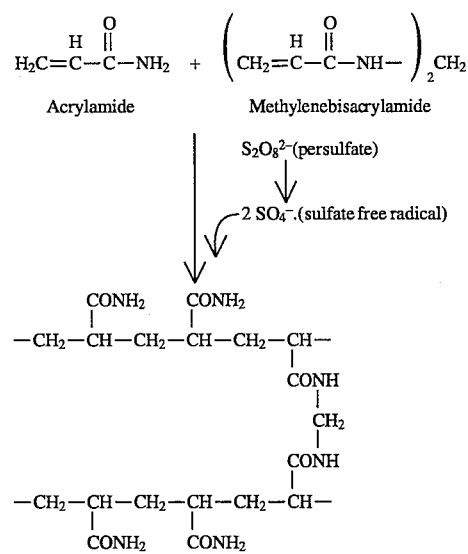

This process and the final product is similar to that of silicone as shown below.

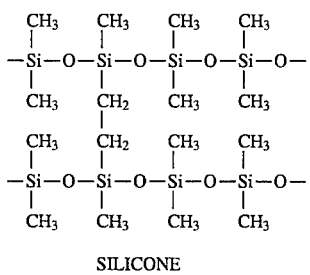

SILICONE

Compounds that can act as free-radical traps inhibit the cross-linking procedure (Bio-Rad Technical Bulletin). Oxygen present in the air is such a compound and can inhibit complete polyacrylamide cross-linking at the gel-air interface. This results in the formation of a thin layer of PPA at the air-gel interface. The PPA is electrophoretically transferred to the nitrocellulose, along with proteins in the gel, upon traditional Western blot transfer.

It was possible that PPA resulted from impurities in certain sources of the acrylamide or varied in reactivity based on the nature of cross-linker molecule employed in acrylamide polymerization (usually bisacrylamide). To test this, PPA was prepared with several sources of acrylamide and with several alternative cross-linker molecules, including acrylamide (Bio-Rad), diallyltartardiamide (Sigma), bisacrylamide (Sigma), acrylamide (Sigma), diacryloylpiperazine (Sigma), and acrylamide/bisacrylamide pre-mix (Bio-Rad). Using an APA line blot assay, both IgG and IgM reactivity to these different PPA products was determined. The reactivity of sera moderately reactive or strongly reactive for PPA did not vary appreciably to different acrylamide sources. However, IgG and IgM reactivity did vary with respect to the specific cross-linker molecule used. In the IgG-APA line blot assay, serum moderately reactive to PPA reacted with diallyltartardiamide (Sigma), bisacrylamide (Sigma) and diacryloylpiperazine (Sigma), and serum strongly reactive to PPA reacted with all six different PPA products, with especially strong reactions to PPA products including acrylamide (Sigma), diacryloylpiperazine (Sigma), and acrylamide bisacrylamide premix (Bio-Rad). Additionally, nonspecific reactivity was observed with partially polymerized polymers made only with bisacrylamide (PPB), as all serum samples, including samples strongly reactive, moderately reactive and negatively reactive to PPA showed a reaction with bisacrylamide (Sigma) in both the IgG-APA line blot assay and the IgM-APA line blot assay.

Degradation of PPB and Optimization of APA-PPB Reactivity

The nonspecific reactivity of partially polymerized bisacrylamide (PPB) demonstrated varied considerably with time and was suspected to be a result of degradation. This hypothesis was tested by making a series of line blot strips containing sera moderately reactive to PPB that had been allowed to sit at room temperature for 0 (day 0), 1 (day 1) and 2 days (day 2). PPB appeared to degrade by the second day (day 2) of sitting at room temperature, as the line blots indicated that the serum samples reacted with PPB on day 0 and day 1, but showed no reaction on day 2. However, a white precipitate was noted in the bottom of the PPB mixture that when resuspended, restored PPB reactivity. This restoration of PPB reactivity was demonstrated when on day 2, following resuspension of the PPB, the line blot indicated that the serum sample reacted with PPB. It was concluded that PPB was not degrading but had continued to polymerize, eventually precipitating out of solution. This explained the granular appearance of PPB in comparison to PPA.

To further characterize PPB, reactivity of PPB with strongly reactive sera was assessed by preparing APA line blots with several dilutions of PPB and assessing the reactivity of these strips with positive sera. The PPB dilutions tested included 1:1, 1:5, 1:10, and 1:20. Undiluted and 5 fold diluted PPB were found to be the most useful concentrations.

Development of the antipolymer antibody (APA) line blot.

A diagnostic test capable of assessing an immunological response to silicone would be useful given the controversy surrounding silicone gel filled breast implants. Therefore, an APA line blot was developed that had increased specificity and sensitivity in detecting APAs. Sera from silicone exposed and non-silicone exposed individuals was tested at primary antibody concentrations of 1:100, 1:200, and 1:400 for reactivity to PPA on APA line blots. PPA dilutions of 1:20, 1:100, 1:500, and 1:2500 were used.

The results were as follows:

(1) PPA strongly reactive (APA positive) sera from silicone-exposed individuals visibly reacted with all dilutions of PPA at all three primary antibody concentrations.

(2) PPA negatively reactive sera (APA negative) from silicone-exposed individuals was nonreactive at the three primary antibody concentrations.

(3) PPA positively reactive sera (APA positive) from non-silicone-exposed individuals was reactive at primary antibody concentrations of 1:100 and 1:200 but not 1:400.

(4) PPA negatively reactive sera (APA negative) from non-silicone exposed individuals was nonreactive at all three primary antibody concentrations.

Based on these observations, the current APA line blot assay was developed. PPA in 5, 25, 125, 625, and 3,125 fold dilutions and PPB in 0 and 5 fold dilutions were line blotted onto nitrocellulose membranes. Assays were performed using PPA strongly positive sera, moderately reactive sera, and negatively reactive sera. The assays demonstrated that at PPA dilutions of 1:5 and 1:25, strongly positive sera and moderately reactive sera showed a reaction, indicating the presence of antipolymer antibodies. Strongly positive sera also reacted at PPA dilutions of 1:125 and slightly reacted at 1:625. Negatively reactive sera showed no reaction at any of the PPA dilutions. For the undiluted PPB, the results were inconclusive as strongly positive, moderately reactive, and negatively reactive sera all showed slight reactions. No reactions were visible for the 5 fold diluted PPB.

Characterization of APAs

It was possible that APA reactivity was directly a function of total immunoglobulin concentration and not the result of specific anti-PPA serum antibodies. To determine if a correlation existed between APAs and total immunoglobulin concentration, total IgG, IgA and IgM immunodiffusion concentration assays were performed (The Binding Site Limited, Birmingham, England) on sera with varying APA reactivity. Total IgG, IgM, and IgA immunoglobulin concentration in mg/L was determined and categorized by isotype according to APA reactivity, including APA strongly reactive (APA+), APA moderately reactive (APA±), and APA negatively reactive (APA−). No correlation was found to exist between the total serum immunoglobulin of any isotype and the level of APA reactivity.

It was also possible that the anti-PPA reactivity of APAs results from non-specific interactions, as sticky antibodies are known to react with many antigens in a non-specific manner not mediated by the F'ab binding domain of the antibody. To establish the nature of APA reactivity, an APA line blot assay was performed. Two PPA strongly-reactive serum samples were digested with immobilized papain into F'c and F'ab subunits (Pierce Laboratories).

Digested APA F'ab fragments were purified by protein-A column chromatography to remove F'c fragments. The remaining PPA reactivity was assessed on APA line blots using anti-F'ab secondary antibody. Undigested strongly reactive sera, non-protein A purified F'ab digested strongly reactive sera, and F'ab containing 1.5 ml elution fractions after F'c fragment removal with protein A chromatography were compared. PPA dilutions of 1:5, 1:25, 1:125, 1:625, and 1:3125, undiluted PPB, and PPB diluted 5 fold were used in the assay.

The results showed that some PPA reactivity was lost as a result of papain digestion, as undigested strongly reactive sera reacted at all PPA concentrations, as well as in undiluted PPB, compared to non-protein A purified, F'ab digested sera, which only showed a reaction at PPA concentrations of 1:5 and 1:25, and slight reactivity at 1:125. However, subsequent to F'c fragment removal with protein A column chromatography, the remaining PPA reactivity appeared to reside predominantly in F'ab purified fractions.

Frequency of APAs in individuals exposed to silicone breast implants.

Exposure to silicone breast implants can result in the manifestation of symptoms and complications that collectively are dissimilar from previously recognized or defined rheumatological diseases and therefore will be uniquely identifiable with the appropriate diagnostic tests. Using a combination of APA line blot techniques, it was determined that the approximately 50% (363/667) of persons reporting complications following silicone breast implantation produced APAs serum antibodies. This was significantly greater than the 7% (7/100) observed in healthy blood donor sera ($p<0.0005$). Sera from patients experiencing other autoimmune complications (SLE, RA, juvenile rheumatoid arthritis, or diffuse scleroderma) demonstrated APA antibodies in less than 10% of the cases. Therefore, anti-polymer antibodies do not seem to be a general marker for autoimmunity. However, patients with the CREST form of scleroderma demonstrated detectable APAs in 50% (10/20) of the cases tested. This is of interest because scleroderma-like symptoms, including tightness of skin, contracture, sclerodactyly, alopecia, edema, telangiectasias, rash, and changes in pigmentation, have frequently been associated with silicone breast implants (Brozena et al., 1988; Vasey et al., 1991; Spiera et al., 1994).

TABLE 1

Anti polymer antibodies (APAs) in recipients of silicone breast implants detectable by Line immunoblotting.

| Donor Group/Diagnosis | # positive /# tested | Percent positive | Significance |
| --- | --- | --- | --- |
| healthy blood donors | 9/100 | 9.0% | |
| silicone implant recipients | 363/667 | 50.7% | $p < 0.0005$[a] |
| Scleroderma (CREST) | 10/20 | 50.0% | $p < 0.0005$ |
| Scleroderma (diffuse) | 1/10 | 10.0% | NSS[b] |
| systemic lupus erythematosus | 13/205 | 6.3% | NSS |
| adult rheumatoid arthritis | 3/92 | 3.3% | NSS |
| juvenile rheumatoid arthritis | 1/11 | 9% | NSS |

[a]student test
[b]NSS = not statistically significant

Correlation of rheumatic symptoms with production of antibodies to PPA.

Patients with complications associated with exposure to silicone from breast implants were 17 times more likely to produce detectable APAs than healthy blood donors (95% confidence limit 7.55–46.69). This percentage is highly relevant to complications from breast implants because not all silicone breast implant recipients who are currently seeking treatment actually are experiencing complications directly resulting from silicone exposure.

EXAMPLE 2

To correlate the anti-polymer antibody assay with the occurrence of specific clinical symptoms, sixty-nine patients with silicone disease as defined by joint aching about the MP's, PIP's, dysesthsias, paresthesias, multiple tender spots including the occupant, upper cervical, epicondyler, hips, knees and ankles, overwhelming fatigue, general malaise and widespread pain were studied. Of the 69 patients, 58 (84.06%) were felt to have silicone disease and 11 (15.94%) were felt to have no disease or localized myofascial discomfort.

Of the 69 patients, 17 patients had other antibodies and may or may not have silicone disease. Of these, 5 patients had well-known rheumatic disease by American College of Rheumatology criteria, including 2 patients with primary Sjögren's syndrome, 1 patient with CREST, 1 patient with seropositive rheumatoid arthritis and 1 patient who met ACR criteria for lupus. There was 1 patient with chronic persistent hepatitis. Four patients had positive rheumatoid factors and 7 patients had anti-thyroid antibodies.

Fifty-eight patients had silicone disease. Of these 58, 38 (65.52%) had a negative antinuclear antibody (ANA) test result, while 20 (34.48%) had a positive ANA result. Eleven patients had no silicone disease. Of the 11, six patients (54.55%) had a negative ANA result, while 5 (45.45%) had a positive result.

Thirty-five out of the 58 patients that had silicone disease tested positive for silicone antibodies, including 22 patients (37.93%) who clearly had the antibodies and 13 (22.41%) who had probable silicone antibodies. The remaining 23 patients (39.66%) with silicone disease had no silicone antibodies.

Thus, roughly sixty percent of the patients with silicone disease had the silicone antibody.

Of the remaining 11 patients without any silicone disease, only 4 patients had a silicone antibody. Seven of the 11 (63.64%) who did not have silicone disease had no silicone antibody. This antibody is a very good predictor of silicone disease since 60% of patients with disease had the antibody.

The antinuclear antibody test was present at a low titer in 20 patients with disease, making it likely to be present in about a third of the patients with silicone disease. Those who had no disease and localized myofascial pain had about 40% antinuclear positive antibodies, making the antinuclear antibody test not a good predictor of silicone disease.

The following tables (Tables 2–4) demonstrate the use of the anti-polymer antibody assay in an ELISA format. The dilution ratio of the antigen, partially polymerized polyacrylamide, attached to each well of a polystyrene 96-well plate is shown in column 1 (left hand column). The serum dilution ratio (1/50, 1/100, etc.) for representative patient samples is shown in the first row at the top of each column. Strong-positive, weak-positive, and negative reacting serum samples were tested. The serum was incubated in the wells containing the antigen, then reacted with a goat-anti-human alkaline phosphatase labelled secondary antibody. The data are presented as the optical density from the signal production system consisting of the reaction of this labelled secondary antibody with the substrate 5-bromo-4-chloro-3-indole phosphate (BCIP) phosphate. Wells containing neither PPA nor serum in the column marked blank are set to zero relative to the other wells.

TABLE 2

STRONG POSITIVE

| PPA Dilution | Serum Dilution | | | |
|---|---|---|---|---|
| | 1/50 | 1/100 | 1/200 | 1/400 |
| 0 | 0.392 | 0.068 | −0.042 | −0.09 |
| 1/15625 | 0.73 | 0.583 | 0.378 | 0.364 |
| 1/3125 | 2.013 | 2.5 | 2.038 | 1.587 |
| 1/625 | 2.5 | 2.5 | 2.5 | 2.5 |
| 1/125 | 2.5 | 2.5 | 2.5 | 2.047 |
| 1/25 | 2.5 | 2.5 | 2.5 | 2.5 |
| 1/5 | 2.5 | 2.5 | 2.5 | 1.373 |
| 1/ | 2.5 | 2.5 | 2.5 | 2.5 |

TABLE 3

WEAK POSITIVE

| PPA Dilution | Serum Dilution | | | |
|---|---|---|---|---|
| | 1/50 | 1/100 | 1/200 | 1/400 |
| 0 | 0.155 | 0.075 | −0.038 | −0.1 |
| 1/15625 | 0.435 | 0.18 | 0.105 | −0.08 |
| 1/3125 | 1.404 | 0.91 | 0.428 | 0.135 |
| 1/625 | 2.062 | 1.536 | 0.735 | 0.34 |
| 1/125 | 2.5 | 2.5 | 1.254 | 0.375 |
| 1/25 | 2.5 | 1.896 | 1.061 | 0.495 |
| 1/5 | 2.5 | 2.5 | 1.45 | 0.668 |
| 1/ | 2.5 | 2.5 | 2.5 | 1.379 |

TABLE 4

NEGATIVE

| PPA Dilution | Serum Dilution | | | |
|---|---|---|---|---|
| | 1/50 | 1/200 | 1/400 | blank |
| 0 | 0.117 | −0.062 | 0 | 0 |
| 1/15625 | 0.366 | −0.1 | 0.02 | 0 |
| 1/3125 | 0.006 | −0.012 | 0.006 | 0 |
| 1/625 | 0.106 | −0.045 | 0.055 | −0.1 |
| 1/125 | 0.01 | −0.098 | 0.008 | −0.1 |
| 1/25 | 0.047 | 0.097 | −0.1 | 0.224 |
| 1/5 | −0.004 | −0.087 | 0.072 | −0.1 |
| 1/ | −0.039 | −0.1 | −0.1 | −0.1 |

CONCLUSION

The detection of APAs in this study may represent immunology cross-reactivity directed against silicone or another component found in breast implants. Alternatively, silicone may function as an adjuvant and/or physically interact with cellular components present in the surrounding connective tissue, such as collagen. This may result in the structural alteration of the silicone or the cellular component so as to antigenically resemble PPA. Silicone, collagen, and PPA are cross-linked polymers. It is possible that any antigenic relationship among these substances results from the type and degree of cross-linking, and not from chemical composition of the polymer.

The observation that exposure to silicone implants does not appear to be necessary for the development of APAs is consistent with this latter hypothesis. About 7% of the healthy population appear to produce antibody that cross-react with PPA. This must be qualified because silicone-containing devices are widely used in medicine, commerce, and industry, and it is possible that our normal blood donors may have been unknowingly exposed to silicone. Alternatively, individuals with pre-existing APAs may be predisposed to complications following silicone implantation, although this has yet to be established. Current attempts are being made to establish the correlation of APAs titer to silicone breast implant complication severity and symptomatology.

Based on the observations with PPA and PPB, it is suspected that APAs react with a heterogeneous polymeric structure (possibly in a circular conformation) composed of acrylamide/bisacrylamide that may antigenically resemble a silicone implant polymer component. Although conjecture, a circular structure may provide the level of complexity necessary to convey antigenicity to a relatively simple polymer structure. Additionally, circular polymer complexes would be resistant to further polymerization and therefore, be more likely present as a partially polymerized component of an acrylamide gel.

The identification of a newly described anti-polymer antibody (APA) that may be associated with silicone related complications was also detailed in this dissertation and was first detected with the HIV-1 Western blot. This led to the partial characterization of the antigen as a polymer of partially polymerized acrylamide (PPA) with specific composition. APAs that react with PPA were shown to be specific, of high titer, independent of total immunoglobulin concentration, and predominantly found in patients with complications related to silicone exposure. Based on these observations, a preliminary diagnostic assay has been developed. Currently, the correlation between seroreactivity on this assay and silicone related autoimmune symptomatology is being assessed.

Although the controversy concerning the relationship between silicone gel filled breast implants and the development of autoimmune disease is not resolved (Gabriel et al., 1994), the results obtained using the anti-polymer antibody line blot assay make a compelling argument that at least some individuals mount a specific anti-polymer immune response subsequent to silicone exposure.

The identification and characterization of non-viral antigens present on the HIV-1 Western blot should help in the interpretation of indeterminate results obtained on the assay. Given that any reactivity on the HIV-1 Western blot assay is considered an indeterminate result regarding a person of uncertain HIV serostatus, the ramifications of reactivity in blood donors are important. The nature of the interplay between viral proteins, cellular proteins and other antigens may provide information relevant to the understanding of mechanisms leading to systemic autoimmune diseases.

REFERENCES

Angell, M. (1992). Breast implants—protection or paternalism? [editorial; comment] [see comments]. *N Engl J Med* 326: 1695–6.

Brozena, S. J., Fenske, N. A., Cruse, C. W., Espinoza, C. G., Vasey, F. B.,Germain, B. F. and Espinoza, L. R. (1988). Human adjuvant disease following augmentation mammoplasty. *Arch Dermatol* 124: 1383–6.

Copeland, M., Kressel, A., Spiera, H., Hermann, G. and Bleiweiss, I.J. (1993). Systemic inflammatory disorder related to fibrous breast capsules after silicone implant removal. *Plast Recontr Surg* 92: 1179–81.

Gabriel, S. E., O'Fallon, W. M., Kurland, L. T., Beard, C. M., Woods, J. E. and Melton, L.3. (1994). Risk of connective-tissue diseases and other disorders after breast implantation [see comments]. *New England Journal of Medicine* 330: 1697–702.

Kessler, D. A. (1992). The basis of the FDA's decision on breast implants. [see comments]. *N Engl T Med* 326: 1713–5.

Kessler, D. A., Merkatz, R. B. and Schapiro, R. (1993). A call for higher standards for breast implants [comment]. *Jama* 270: 2607–8.

Miyoshi, K., Miyamia, T., Kobayshi, Y. and al., e. (1964). Hypergammaglobulinemia by prolonged adjuvancy in man: Disorders developed after augmentation mammography. *Jpn J. Med.* 9: 21–22.

Miyoshi, K., Shiragami, H. and Yoshida, K. (1973). Adjuvant diseases in man. *Clin. Immunol.* 5: 785–794.

Seleznick, M. J., Martinez-Osuna, P., Espinoza, L. R. and Vasey, F. B. (1991). Is silicone associated with connective tissue disease? *J Fla Med Assoc* 78: 85–7.

Spiera, H. and Kerr, L. D. (1993). Scleroderma following silicone implantation, a cumulative experience of 11 cases. *J Rheumatol* 20: 958–61.

Spiera, R. F., Gibofsky, A. and Spiera, H. (1994). Silicone gel filled breast implants and connective tissue disease: an overview. [Review]. *Journal of Rheumatology* 21: 239–45.

Touchette, N. (1992). Silicone implants and autoimmune diseases: Studies fail to gel. *J. NIH Res* 4: 49–52.

Vasey, F. B., Espinoza, L. R., Martinez-Osuna, P., Seleznick, M. J., Brozena, S. J. and Penske, N. A. (1991). Silicone and rheumatic disease: replace implants or not? [letter; comment]. *Arch Dermatol* 127: 907.

What is claimed is:

1. A method to aid the diagnosis of silicone related disease in a patient, comprising the steps of:

obtaining a sample of serum from the patient;

detecting an antipolymer antibody in said sample, wherein said antibody specifically binds with partially polymerized acrylamide; and correlating the presence or absence of the antibody with silicone related disease, where if:

(i) said patient has no polymeric implant, then the presence of said antibody indicates that the patient may have a condition predisposing to silicone related disease;

(ii) said patient has a polymeric implant, then the presence of said antibody indicates that the patient may have silicone related disease;

(iii) said patient has a polymeric implant, then the absence of said antibody indicates that the patient may not have silicone related disease;

(iv) said patient has a polymeric implant and has been previously diagnosed as having undifferentiated rheumatoid disease selected from the group consisting of silicone related disease, atypical connective tissue disease, atypical rheumatic syndrome, nonspecific autoimmune condition, or overt autoimmune diseases, then the presence of said antibody indicates said rheumatoid disease may be silicone related disease; and (v) said patient has no polymeric implant and has previously been diagnosed as having an undifferentiated rheumatoid disease selected from the group consisting of silicone related disease, atypical connective tissue disease, atypical rheumatic syndrome, nonspecific autoimmune condition, or overt autoimmune diseases, then the absence of said antibody indicates said rheumatoid disease may be predisposing to silicone related disease.

2. A method of detecting antipolymer antibody in body fluid sample from a patient, comprising the steps of:

(a) obtaining a sample of body fluid from said patient;

(b) reacting said sample with partially polymerized acrylamide for a time and under conditions sufficient for said antibody to specifically bind to said partially polymerized acrylamide, thereby forming a complex; and (c) detecting the presence or absence of said complex as an indication of the presence or absence of said antibody in said sample.

3. A method of detecting antipolymer antibody in a body fluid sample from a patient, comprising the steps of:

(a) reacting said body fluid sample with partially polymerized acrylamide attached to a solid phase, for a time and under conditions sufficient for said antibody in said body fluid sample to specifically bind to said partially polymerized acrylamide forming a complex on said solid phase; and (b) reacting said complex with an indicator reagent, wherein said indicator reagent comprises a binding member that is specific for a human antibody and conjugated to a detectable label, for a time and under conditions sufficient to form a labeled ternary complex on said solid support; and (c) detecting the presence or absence of said labeled ternary complex as an indication of the presence or absence of said antibody in said body fluid sample.

4. A diagnostic kit comprising, in separate packaging:

a) an antigen comprising partially polymerized acrylamide attached to a solid surface;

b) an indicator reagent, wherein said indicator reagent comprises a binding member that is specific for an antibody and conjugated to a detectable label;

c) a wash composition for separating uncomplexed materials from a complex of an antibody from a human serum sample; and d) a composition for providing a colorimetric or chemiluminescent signal in the presence of an enzyme label.

5. A diagnostic kit comprising, in separate packaging:

an antigen comprising partially polymerized acrylamide immobilized on a solid phase material; and an indicator reagent capable of indicating the presence or absence of antibodies bound to said antigen.

* * * * *